(12) United States Patent
Thistle

(10) Patent No.: US 7,833,263 B2
(45) Date of Patent: Nov. 16, 2010

(54) HYBRID VASCULAR GRAFT REINFORCEMENT

(75) Inventor: Robert C. Thistle, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 260 days.

(21) Appl. No.: 11/096,686

(22) Filed: Apr. 1, 2005

(65) Prior Publication Data

US 2006/0224236 A1  Oct. 5, 2006

(51) Int. Cl.
*A61F 2/06* (2006.01)
(52) U.S. Cl. ............ 623/1.32; 623/1.33; 623/1.35
(58) Field of Classification Search ............ 623/1.32, 623/1.44, 1.13, 1.15, 1.28, 1.29, 1.35, 1.27, 623/1.33, 1.49–1.54, 1.11, 1.12, 1.23, 1.34
See application file for complete search history.

(56) References Cited

U.S. PATENT DOCUMENTS

| | | | |
|---|---|---|---|
| 5,116,360 A | | 5/1992 | Pinchuk et al. |
| 5,163,951 A | | 11/1992 | Pinchuk et al. |
| 5,843,158 A | | 12/1998 | Lenker et al. |
| 5,871,536 A | * | 2/1999 | Lazarus ............ 623/1.13 |
| 5,910,168 A | * | 6/1999 | Myers et al. ............ 623/1.44 |
| 6,015,429 A | | 1/2000 | Lau et al. |
| 6,117,168 A | * | 9/2000 | Yang et al. ............ 623/1.44 |
| 6,171,688 B1 | * | 1/2001 | Zheng et al. ............ 428/313.5 |
| 6,187,033 B1 | | 2/2001 | Schmitt et al. |
| 6,238,432 B1 | | 5/2001 | Parodi |
| 6,283,991 B1 | * | 9/2001 | Cox et al. ............ 623/1.13 |
| 6,554,855 B1 | | 4/2003 | Dong |
| 6,689,162 B1 | | 2/2004 | Thompson |
| 2003/0009211 A1 | | 1/2003 | DiCarlo |
| 2003/0017775 A1 | | 1/2003 | Sowinski et al. |

(Continued)

FOREIGN PATENT DOCUMENTS

WO        WO9937242        *    1/1999

(Continued)

OTHER PUBLICATIONS

PCT Notification of Transmittal of the International Search Report and the Written Opinion of the International Searching Authority, or the Declaration for International Application No. PCT/US2006/011529, Jul. 5, 2006 (2 pages).

(Continued)

*Primary Examiner*—Corrine M McDermott
*Assistant Examiner*—Suba Ganesan
(74) *Attorney, Agent, or Firm*—Vidas, Arrett & Steinkraus P.A.

(57) ABSTRACT

An implantable vascular graft includes an outer tube structure formed of a textile material, and an inner tube structure formed of a non-textile material. The inner tube structure is within the outer tube structure in coaxial relation therewith. One or both of the outer and inner tube structures have deformable reinforced portions incorporated therein. The deformable reinforced portions provide for conformance of the associated one or both of the outer and inner tube structures to a vessel of a patient. An implantable laminate prosthesis includes a first layer structure formed of textile material, and a second layer structure formed of non-textile material. The first and second layer structures are secured together in laminating relation. The first or second layer structure has a reinforced portion.

13 Claims, 4 Drawing Sheets

U.S. PATENT DOCUMENTS

| | | |
|---|---|---|
| 2003/0028239 A1 | 2/2003 | Dong |
| 2003/0088305 A1* | 5/2003 | Van Schie et al. .......... 623/1.12 |
| 2003/0139806 A1 | 7/2003 | Haverkost et al. |
| 2003/0204241 A1 | 10/2003 | Dong |
| 2004/0215337 A1 | 10/2004 | Hain et al. |

FOREIGN PATENT DOCUMENTS

| | | |
|---|---|---|
| WO | WO 03/103736 | 12/2003 |
| WO | WO 2006/041607 | 4/2006 |

OTHER PUBLICATIONS

PCT International Search Report for International Application No. PCT/US2006/011529, Jul. 5, 2006 (5 pages).

PCT Written Opinion of the International Searching Authority for International Application No. PCT/US2006/011529, Jul. 5, 2006 (6 pages).

U.S. Appl. No. 10/876,212, filed Jun. 24, 2004, Dong, USPTO Filing Receipt, specification and drawings.

* cited by examiner

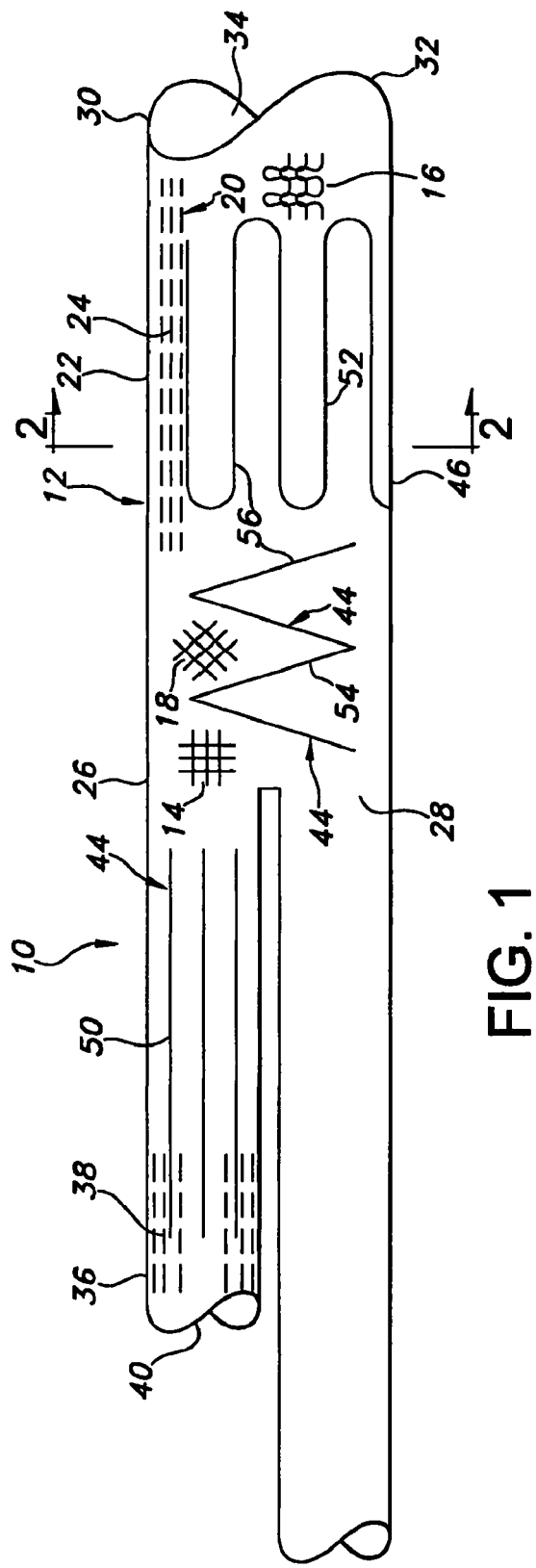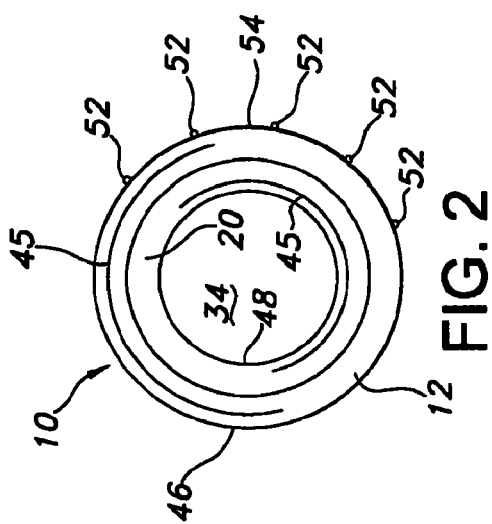

HYBRID VASCULAR GRAFT REINFORCEMENT

FIELD OF THE INVENTION

The present invention relates generally to a hybrid vascular graft including an inner tube formed of non-textile material, such as polytetrafluoroethylene (PTFE), and an outer tube formed of textile material. More specifically, the present invention relates to such a vascular graft having additional materials secured to the outer and inner tubes for reinforcement thereof.

BACKGROUND OF THE INVENTION

Implantable vascular grafts are used in medical applications for the treatment of diseased or damaged blood vessels, such as arteries and veins. Such treatment may be necessitated by conditions in the arteries and veins, such as a stenosis, thrombosis, occlusion or aneurysm. A vascular graft may be used to repair, replace, or otherwise correct a diseased or damaged blood vessel.

A vascular graft may be a tubular prosthesis for replacement or repair of a damaged or diseased blood vessel. To maximize the effectiveness of such a prosthesis, it should be designed with characteristics which closely resemble that of the natural body lumen which is being repaired or replaced by the prosthesis.

An implantable vascular graft may be a multi-layered composite. The multi-layered composite may include a first layer formed of a textile material and a second layer formed of expanded polytetrafluoroethylene (ePTFE) having a porous microstructure defined by nodes interconnected by fibrils. An elastomeric bonding agent is applied to either the first or the second layer and disposed within the pores of the microstructure for securing the first layer to the second layer. An implantable vascular graft may therefore include an ePTFE-lined textile graft, an ePTFE graft, covered with a textile covering, or a vascular patch including a textile surface and an opposed ePTFE surface. Such a vascular graft may include additional ePTFE and/or textile layers.

The ePTFE may be formed from extruded tubes. PTFE is particularly suitable as an implantable prosthesis as it has good biocompatibility and low thrombogenicity. ePTFE has a microporous structure which allows natural tissue ingrowth and cell endothelization once implanted in the vascular system. This contributes to long term healing and patency of the graft.

A hybrid vascular graft may be used in the vascular system, urogenital tract and bile duct, as well as in a variety of other applications in the body. A hybrid vascular graft may be reinforced to open and support various lumens in the body. Such a hybrid vascular graft may be used for the treatment of stenosis, strictures and aneurysms in blood vessels, such as arteries and veins. Such treatments include implanting the vascular graft within the blood vessel to open and/or reinforce collapsing or partially occluded sections of the vessel.

A hybrid vascular graft may be reinforced by providing a stent between the outer layer formed of textile and the inner tubular layer formed of non-textile, such as ePTFE material. Such a composite structure is disclosed in FIGS. 18 and 20 and the related text of U.S. Patent Application Publication No. U.S. 2003/0204241. The entire disclosure of U.S. Patent Application Publication No. U.S. 2003/0204241 is hereby incorporated by reference herein. A stent constituted by a helical coil is disclosed in FIG. 8 and the related text of U.S. Patent Application Publication No. US 2003/0204241.

The reinforcement provided by a stent, such as a helical coil, between the outer and inner tubes of a hybrid vascular graft is generally uniform in the longitudinal and radial directions along the vascular graft. Such uniformity is advantageous for some uses of the vascular graft. However, for other uses, it is preferable for the reinforcement to vary in the longitudinal and radial directions along the vascular graft.

A stent, such as a helical coil, located between the outer and inner tubes of a hybrid vascular graft is typically bonded to the tubes. Accordingly, assembly of such a vascular graft may include handling the stent in addition to the outer and inner tubes, positioning the stent relative to the tubes before the bonding together of the tubes, and securing the stent to the tubes. This may add complexity to and require additional effort for the assembly of the vascular graft. Additionally, the material of the stent must normally be compatible with materials of outer and inner layers, and possibly with the body of the patient. This may limit the type of material which is suitable for the stent. Additionally, it may be desirable to bond the outer and inner tubes together before attachment of the stent thereto.

SUMMARY OF THE INVENTION

The implantable vascular graft of the present invention includes an outer tube structure formed of a textile material, and an inner tube structure formed of a non-textile material. The inner tube structure is within the outer tube structure in coaxial relation therewith. One or both of the outer and inner tube structures have deformable reinforced portions incorporated therein. The deformable reinforced portions provide for conformance of the associated one or both of the outer and inner tube structures to a vessel of a patient. The textile material may be weaved, knitted or braided.

The vascular graft may be reinforced by various materials secured to or by configurations of one or both of the outer and inner tube structures. These materials and configurations may be used individually or in combination with the vascular graft. One such technique for reinforcing the vascular graft includes the bonding of reinforcing material to one or both of the tube structures. Additionally, the textile material of the outer tube may be knitted, weaved or braided which provides further reinforcement.

A further technique for reinforcing the vascular graft is to secure reinforcing material to the outer surface of the outer tube structure or to the inner surface of the inner tube structure. This enables the outer and inner tube structures to be secured together before the attachment of the reinforcing material thereto. This may be advantageous, for example, by allowing the bonding together of the tube structures before the determination of specific reinforcing material to be secured thereto.

An additional technique for reinforcing the vascular graft is to bond reinforcing material to one or both of the outer or inner tube structures, where the reinforcing material is applied to the tube structure or structures in a flowable condition such that, subsequent to the application, the reinforcing material rigidities. The reinforcing material is further secured to one or both of the tube structures by filament material which is stitched to the reinforcing material and to the tube structure or structures to which the reinforcing material is applied.

A further technique for reinforcing the vascular graft is to crimp at least a portion of one or both of the outer and inner tube structures. The crimping provides reinforcement to the vascular graft without requiring the addition of reinforcing material to either the outer or inner tube structures. This simplifies the vascular graft such as by not requiring the identification of a composition for the stiffening material which is compatible with the materials of the outer and inner tube structures.

An additional technique for reinforcing the outer and inner tube structures is to secure a highly absorbent material to one or both of the structures. The securing of the highly absorbent material to one or both of the tube structures may be provided by an adhesive or stitching.

A further technique for reinforcing the vascular graft is to secure the reinforcing material within a channel which is formed on one or both of the outer or inner tube structures. A further technique for reinforcing the outer and inner tube structures is to bond a stiffening rib formed of ePTFE or adhesive material, to one or both of the structures.

The present invention further provides for an implantable laminate prosthesis including a first layer structure formed of a textile material, and a second layer structure formed of a non-textile material. The first and second layer structures are secured together in laminating relation to one another. The first or second layer structure has a reinforced portion which provides support to resist deformation of the laminate prosthesis. The laminate prosthesis may be reinforced by materials and configurations which correspond to the materials and configurations which provide reinforcement to the vascular graft described herein above.

The composite multi-layered implantable structures of the vascular graft and laminate prosthesis are designed to take advantage of the inherent beneficial properties of the materials forming each of the tube and layer structures. The textile tube and layer structures provide for enhanced tissue ingrowth, high suture retention strength and longitudinal compliance for ease of implantation. The non-textile tube and layer structures formed of a PTFE material provides the beneficial properties of sealing the textile tube and layer structures without the need for coating the textile tube and layer structures with a sealant such as collagen. The sealing properties of the non-textile tube and layer structures formed of PTFE material allow the wall thickness of the textile tube and layer structures to be minimized. Further, the non-textile tube and layer structures formed of PTFE material exhibit enhanced thrombo-resistance upon implantation. Moreover, an elastomeric bonding agent, which may be used to secure together the textile and non-textile tube and layer structures, may add further puncture-sealing characteristics to the vascular graft and laminate prosthesis.

These and other features of the invention will be more fully understood from the following description of specific embodiments of the invention taken together with the accompanying drawings.

BRIEF DESCRIPTION OF THE DRAWINGS

In the drawings:

FIG. 1 is a side elevation view of an implantable vascular graft of the present invention, the graft being shown as having an outer tube structure formed of textile material which is illustrated in alternative embodiments as being knitted, weaved and braided;

FIG. 2 is a cross-sectional view of the implantable vascular graft of FIG. 1 in the plane indicated by line 2-2 of FIG. 1;

Corresponding reference characters indicate corresponding parts throughout the several views of the drawings.

DETAILED DESCRIPTION OF THE INVENTION

Figure 3:
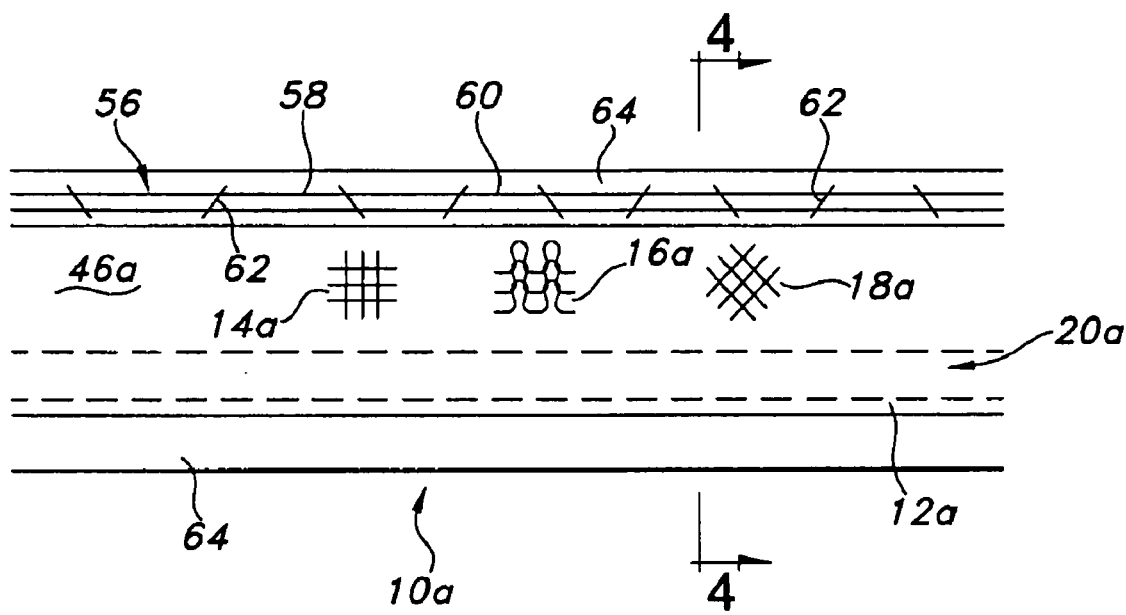
FIG. 3 is a side elevation view of an alternative second embodiment of the implantable vascular graft of FIG. 1, the graft being shown as having an outer tube structure formed of textile material which is illustrated in alternative embodiments as being knitted, weaved and braided.

Referring to the drawings and more particularly to FIGS. 1 and 2, an implantable vascular graft 10 is shown as having an outer tube structure 12 formed of a textile material, which may be knitted, weaved, or braided in alternative embodiments. These alternative embodiments are indicated in FIG. 1 by portions of the outer tube structure 12 being illustrated as weaved 14, knitted 16, and braided 18. It will be understood that the textile of the outer tube structure 12 is typically formed entirely as either weaved 14, knitted 16, and braided 18. It is possible for the outer tube structure 12 to have sections which differ as between weaved 14, knitted 16, and braided 18. Examples of textile material which is weaved 14, knitted 16, and braided 18 are contained in U.S. patent application Ser. No. 10/876,212 filed in the U.S. Patent and Trademark Office on Jun. 24, 2004. The entire disclosure of U.S. patent application Ser. No. 10/876,212 is hereby incorporated by reference herein. The vascular graft 10 has an inner tube structure 20 formed of a non-textile material which, in a preferred embodiment, is PTFE material.

The outer and inner tube structures 12, 20 have respective trunk portions 22, 24 including corresponding opposite ends 26, 28, 30, 32. The trunk portion 24 of the inner tube structure 20 has an interior region 34. The structures 12, 20 have respective pairs of leg portions 36, 37. The leg portions 36, 37 of the inner tube structure 20 have respective interior regions 40. The leg portions 36, 37 extend from adjacent ends of the respective trunk portions 22, 24 such that the interior regions 40 of the leg portions communicate with the interior region 34 of the trunk portion.

The inner tube structure 20 is secured within the outer tube structure 12 in coaxial relation therewith. The securing of the inner tube structure 20 within the outer tube structure 12 results in the deformation of the outer or inner tube structure producing equivalent deformation in the other of the structures.

A preferred technique for securing the outer and inner tube structures 12, 20 together is to incorporate into one or both of the tube structures a bonding material which extends between the inner and outer tube structures. Typically, such bonding material bridges the inner surface of the outer tube structure 12 and the outer surface of the inner tube structure 20.

The bonding material may be incorporated into the outer tube structure 12 by the bonding material being one or more filament structures which are knitted, weaved or braided with the textile material of the outer tube structure. Such filament structures may have attachment properties which are dormant until activated by the filament structures being subjected to a specific condition. Consequently, prior to the activation of the attachment properties of the filament structures, the filament structures do not interfere with the positioning of the inner tube structure 20 within the outer tube structure 12. When the outer and inner tube structures 12, 20 are properly positioned relative to one another, the attachment properties of the filament structures are activated by the filament structures being subjected to a specific condition, such as by heating or sintering. This secures the outer and inner tube structures 12, 20 together. The filament structures may be an adhesive material such as a fluorinated polymer. Alternatively, the filament structures may be PTFE which melts during processing, such as during heating or sintering of the outer and inner tube structures 12, 20. Such melting results in the PTFE flowing into contact with the inner tube structure 20. After completion of the processing, the PTFE solidifies and remains in contact with both the outer and inner tube structures 12, 20 for securing the tube structures to one another.

In an alternative embodiment, the outer and inner tube structures 12, 20 may be secured to one another by a bonding material located between the tube structures and secured thereto. Such a bonding material may be located between the inner surface of the outer tube structure 12 and the outer surface of the inner tube structure 20. The bonding material may be an adhesive, or the polycarbonate urethane which has been sold under the trademark CORETHANE® that is used as an adhesive.

One or both of the outer and inner tube structures 12, 20 has one or more reinforced portions 44. The reinforced portions 44 may have reinforcing material 45 incorporated into one or both of the outer and inner tube structures 12, 20, as indicated in FIG. 2. The incorporation of the reinforcing material 45 into one or both of the outer and inner tube structures 12, 20 may be according to the disclosures of U.S. Pat. Nos. 5,843,158, 6,015,429 and 6,689,162, and U.S. patent application Ser. No. 10/876,212. The entire disclosures of U.S. Pat. Nos. 5,843,158, 6,015,429 and 6,689,162 are each hereby incorporated by reference herein. The reinforcing material 45 may have a filament structure and may be knitted, weaved, braided or otherwise incorporated into the textile material of the outer tube structure 12.

Alternatively, or in addition to the reinforcing material 45, the reinforced portions 44 may include a reinforcing material which is added and secured to one or both of the outer and inner tube structures 12, 20. Such a reinforcing material may be an adhesive of the type used to bond together the structures 12, 20 or various polymers. Such a reinforcing material may be applied to one or both of the outer and inner tube structures 12, 20 in a flowable condition for the securing of the reinforcing material thereto. Such a reinforcing material may rigidify or harden shortly after the application thereof to the structures 12, 20 resulting in bonding thereto of the reinforcing material. Also, the reinforcing material may be a stiffening rib formed of ePTFE or adhesive material. Alternatively, the reinforcing material may be a highly absorbent material formed as a rope or cord which, when contacted by liquids such as bodily fluids, expands and stiffens. The reinforcing material, such as the stiffening rib and highly absorbent material, is secured to one or both of the outer and inner tube structures 12, 20, such as by one or both of adhesive bonding and stitching.

Alternatively, or in combination with the reinforcing material, the reinforced portions 44 may be provided by crimping or pleating the outer surface 46 of the outer tube structure 12, or the inner surface 48 of the inner tube structure 20. The crimping may be maintained by the stiffness of the material, a chemical additive such as a resin, stitching, or a combination thereof.

In a preferred embodiment, the reinforced portions 44 are elongate. The reinforced portions 44 may have various shapes, such as the straight, serpentine, and saw-tooth configurations 50, 52, 54 shown in FIG. 1. The reinforced portions 44 may vary in the longitudinal and circumferential directions, and in combinations thereof.

Figure 4:
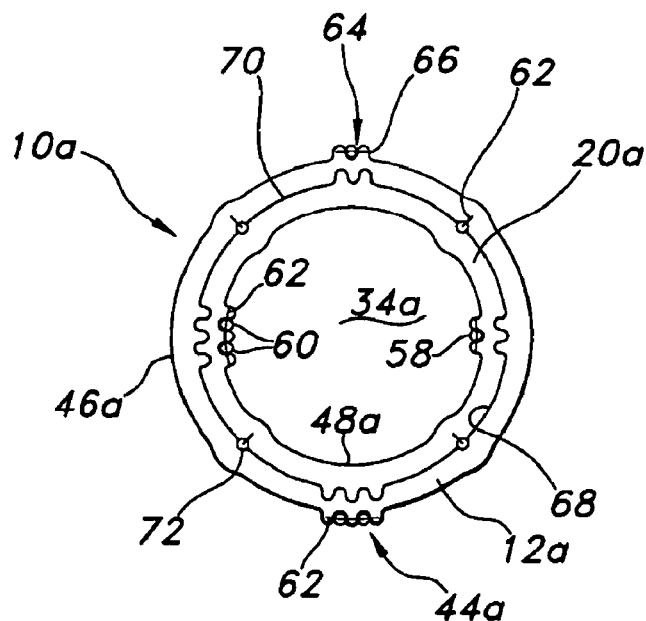
FIG. 4 is a cross-sectional view of the implantable vascular graft of FIG. 3 in the plane indicated by line 4-4 of FIG. 3, the outer and inner tube structures being shown as having channels.

A vascular graft 10a having reinforced portions 44a including reinforcing material 56 is shown in FIGS. 3 and 4. FIGS. 3 and 4 are views which correspond generally to FIGS. 1 and 2. Parts illustrated in FIGS. 3 and 4 which correspond to parts illustrated in FIGS. 1 and 2 have, in FIGS. 3 and 4, the same reference numeral as in FIGS. 1 and 2 with the addition of the suffix "a".

The reinforcing material 56 may be provided by one or more stiffening ribs 58 or highly absorbent materials 60. The stiffening ribs 58, highly absorbent materials 60, and other reinforcing material are secured to one or both of the outer or inner tube structures 12a, 20a, such as by being adhesively bonded thereto. Alternatively, or in combination with the adhesive bonding, the stiffening ribs 58, highly absorbent materials 60, and other reinforcing materials may be stitched to the outer or inner tube structures 12a, 20a by filament material 62, such as suture material.

The stiffening ribs 58, highly absorbent materials 60, and other reinforcing material are supported within channels 64 which extend from the outer surface 46 of the outer tube structure 12a and from the inner surface 48 of the inner tube structure 20a. The channels 64 are formed by respective pairs of folded portions 66 of the structures 12a, 20a. The folded portions 66 may be formed by pinching the inner surface 68 of the outer tube structure 12a and by pinching the outer surface 70 of the inner tube structure 20a. The respective pairs of folded portions 66 are parallel to one another and perpendicular to the adjoining surface of the structures 12a, 20a to define the sides of a corresponding channel 64.

The vascular graft 10a may include internal reinforcing material 72 located between the outer and inner tube structures 12a, 20a. The internal reinforcing material 72 may be constituted by one or more stiffening ribs, highly absorbent materials and other reinforcing material having generally the same nature and composition as the reinforcing material 56. The internal reinforcing material 72 may be secured to one or both of the outer and inner tube structures 12a, 20a, such as by being adhesively bonded thereto. Alternatively, or in combination with the adhesive bonding, the internal reinforcing material 72 may be stitched to the outer or inner tube structure 12a, 20a by filament material 62, such as suture material. The internal reinforcing material 72 may be applied to the structures 12a, 20a in a flowable condition, in a similar manner as described herein above for the reinforcing material 56 shown in FIGS. 1 and 2.

Figure 5:
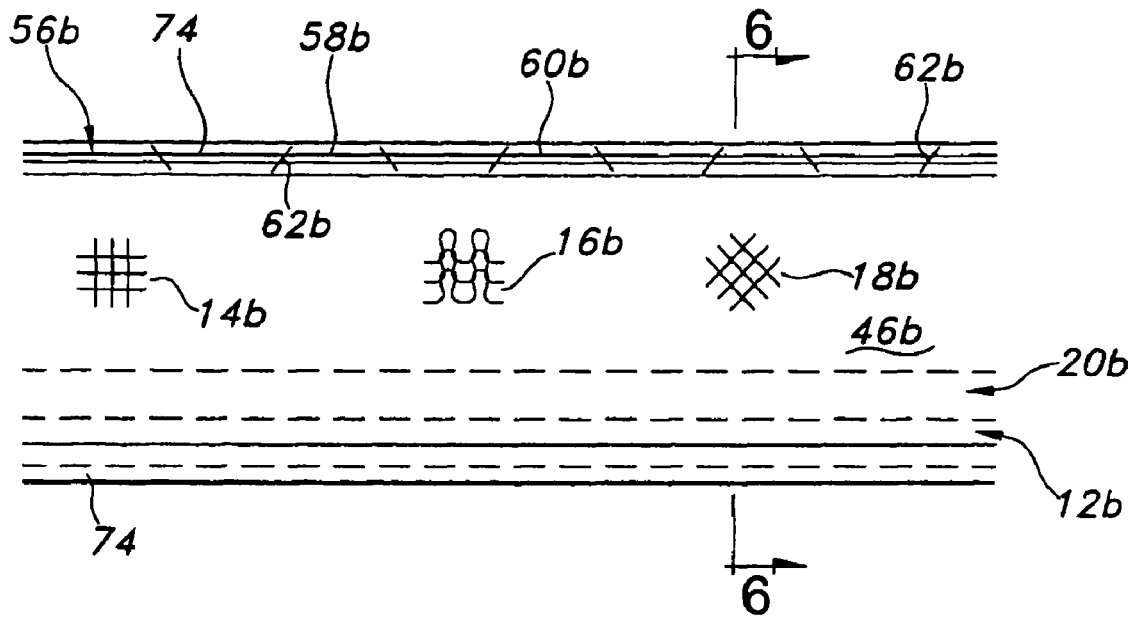
FIG. 5 is a side elevation view of an alternative third embodiment of the implantable vascular graft of FIG. 1, the graft being shown as having an outer tube structure formed of textile material which is illustrated in alternative embodiments as being knitted, weaved and braided.
Figure 6:
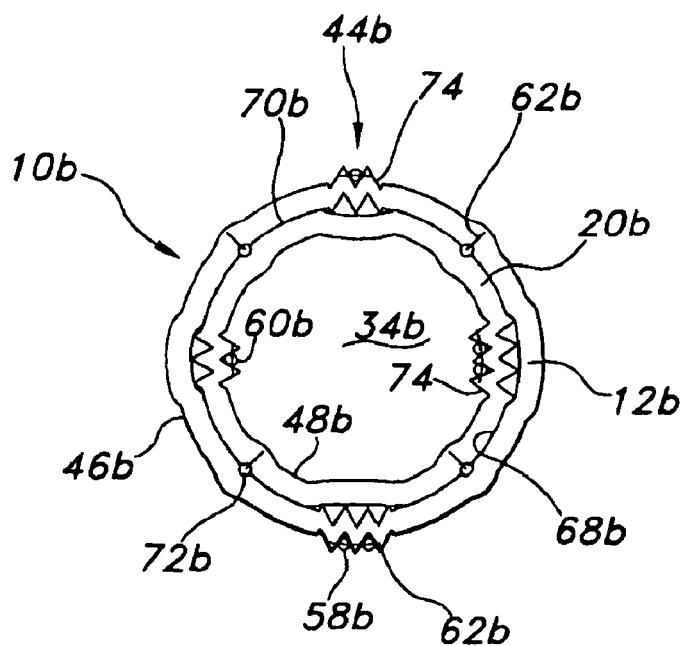
FIG. 6 is a cross-sectional view of the implantable vascular graft of FIG. 5 in the plane indicated by line 6-6 of FIG. 5, the outer and inner tube structures being shown as being crimped.

A vascular graft 10b having reinforced portions 44b provided by crimping 74 one or both of the outer and inner tube structures 12b, 20b is shown in FIGS. 5 and 6. FIGS. 5 and 6 are views which correspond generally to FIGS. 1 and 3, and FIGS. 2 and 4, respectively. Parts illustrated in FIGS. 5 and 6 which correspond to parts illustrated in FIGS. 1 to 4 have, in FIGS. 5 and 6, the same reference numeral as in FIGS. 1 to 4 with the addition of the suffix "b".

The crimping 74 may be on one or both of the outer surface 46b of the outer tube structure 12b and the inner surface 48b of the inner tube structure 20b. Reinforcing material 56b may be secured to the crimping 74 such as by being adhesively bonded thereto. Alternatively, or in combination with the adhesive bonding, the reinforcing material 56b may be stitched to the crimping 74 by filament material 62b, such as suture material.

The vascular graft 10b may include internal reinforcing material 72b located between the outer and inner tube structures 12b, 20b. The internal reinforcing material 72b may be of generally the same nature and composition as the internal reinforcing material 72 shown in FIGS. 3 and 4. The reinforcing material 72b may be secured to one or both of the outer and inner tube structures 12b, 20b in generally the same manner as the reinforcing material 72 shown in FIGS. 3 and 4.

The vascular graft 10, 10a, 10b is suitable for implantation within the body of a patient. The reinforced portions 44, 44a, 44b may be deformable such that the associated portions of the outer and inner tube structures 12, 12a, 12b, 20, 20a, 20b are conformable to a vessel within the body of a patient. Resistance to deformation is provided to the portions of the structures 12, 12a, 12b, 20, 20a, 20b having the reinforced portions 44, 44a, 44b. The reinforced portions 44, 44a, 44b may be configured to resist deformation of the annular cross-sections of the outer and inner tube structures 12, 12a, 12b, 20, 20a, 20b. This resistance to deformation of the annular cross-sections of the structures 12, 12a, 12b, 20, 20a, 20b may be sufficient to facilitate expansion or removal of one or more obstructions in a vessel during implantation therein of the vascular graft 10, 10a, 10b. Alternatively, or in addition to this resistance provided by the reinforced portions 44, 44a, 44b, the reinforced portions may be configured to resist longitudinal deformation of the structures 12, 12a, 12b, 20, 20a, 20b including both elongation and compression thereof.

The resistance to longitudinal deformation and deformation of the annular cross-sections of the structures 12, 12a, 12b, 20, 20a, 20b may be affected by the textile material of the outer tube structure. For example, textiles which are weaved typically provide greater resistance to elongation as compared to textiles which are knitted or braided. A textile which is knitted may be the material for a tube structure of a vascular graft 10, 10a, 10b, which is similar to that disclosed in U.S. Patent Application Publication No. US 2003/0204241. Accordingly, the resistance to deformation of the vascular graft 10, 10a, 10b may be controllably varied by selecting a specific textile pattern, such as knitted, weaved or braided, as the material for the outer tube structure 12, 12a, 12b.

Figure 7:
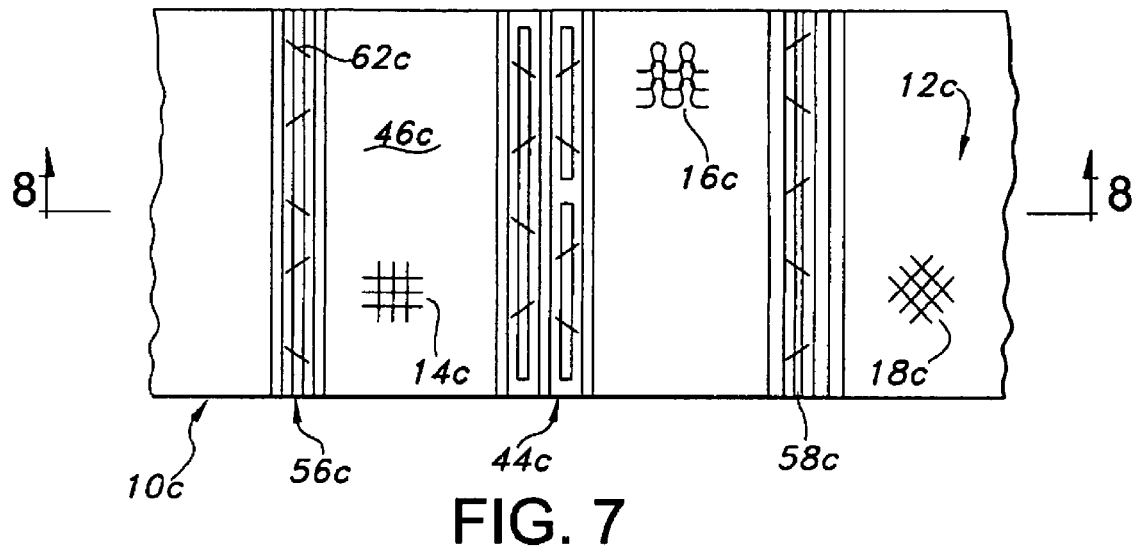
FIG. 7 is a plan view of an implantable laminate prosthesis of the present invention, the prosthesis being shown as having a first layer structure formed of textile material which is illustrated in alternative embodiments as being knitted, weaved or braided.
Figure 8:
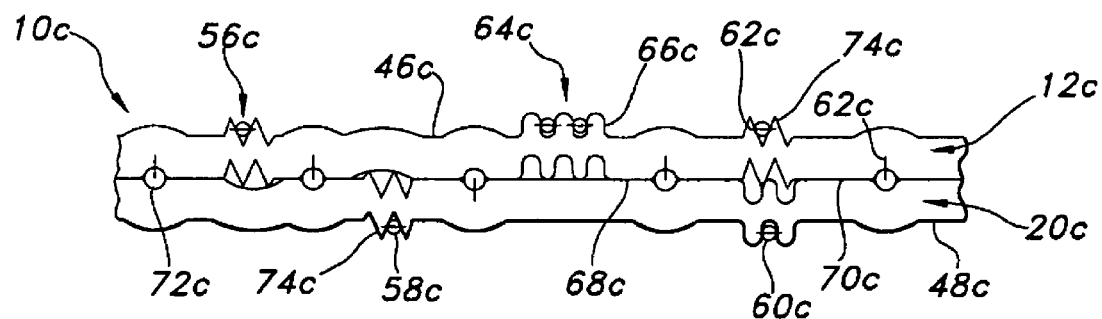
FIG. 8 is a cross-sectional view of the implantable laminate prosthesis of FIG. 7 in the plane indicated by line 8-8 of FIG. 7, the first and second layer structures being shown as having channels and being crimped.

An implantable laminate prosthesis 10c, including a first layer structure 12c secured to a second layer structure 20c in laminating relation thereto, is shown in FIGS. 7 and 8. The first layer structure 12c is formed of textile material, and the second layer structure 20c is formed of non-textile material. In this and other respects, the structures 12c, 20c correspond to the outer and inner tube structures 12, 12a, 12b, 20, 20a, 20b. In further respects, the first and second layer structures 12c, 20c differ from the structures 12, 12a, 12b, 20, 20a, 20b such as, for example, the tubular shape thereof as compared to the planar shape of the first and second layer structures. Accordingly, FIGS. 7 and 8 are views which correspond generally to FIGS. 1, 3 and 5, and to FIGS. 2, 4 and 6, respectively. Parts illustrated in FIGS. 7 and 8 which correspond to parts illustrated in FIGS. 1 to 6 have, in FIGS. 7 and 8, the same reference numeral as in FIGS. 1 to 6 with the addition of the suffix "c".

The laminate prosthesis 10c has reinforced portions 44c which correspond generally to the reinforced portions 44, 44a, 44b. Accordingly, the laminate prosthesis 10c may include reinforcing material 56c secured to one or both of the first or second layer structures 12c, 20c. Additionally, the laminate prosthesis 10c may include channels 64c in which the reinforcing material 56c is supported and secured. Also, one or both of the structures 12c, 20c may be crimped 74c and reinforcing material 56c may be secured thereto. Internal reinforcing material 72c may be located between the first and second layer structures 12c, 20c and secured thereto, as shown in FIG. 8. The reinforcing material 56c, 72c provides support to resist deformation of the laminate prosthesis 10c.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An implantable vascular graft comprising:
   an outer tube structure formed of a textile material;
   an inner tube structure formed of a non-textile material, said inner tube structure being secured to said outer tube structure such that said inner tube structure is within said outer tube structure in coaxial relation therewith;
   a first flowable reinforcing material applied to one of said outer or inner tube structures such that, subsequent to said application, said first reinforcing material rigidifies and has a configuration of an elongate rib having a serpentine configuration;
   a second flowable reinforcing material applied to the other of said outer or inner tube structures such that subsequent to said application, said second reinforcing material rigidifies and has a configuration of an elongate rib having a saw-tooth configuration;
   a filament material stitched to at least one of said reinforcing materials and to said outer or inner tube structure for securing the at least one of said reinforcing materials thereto such that the at least one of said reinforcing materials extends through a limited section of a circumference of said outer or inner tube structure wherein the at least one of said reinforcing materials has opposite ends between which a circumferential portion of said outer or inner tube structure is located; and
   a bonding material having a first state and a second state, in said first state said bonding material comprises a plurality of filaments woven through said outer tube structure, wherein in said first state, said inner tube structure is moveable relative to said outer tube structure; in said second state, said bonding material securingly bonds said outer tube structure to said inner tube structure.

2. An implantable vascular graft according to claim 1, wherein said outer and inner tube structures each comprise: a trunk portion having opposite ends, said trunk portion of said inner tube structure having an interior region; and a pair of leg portions, said leg portions of said inner tube structure each having an interior region, said leg portions extending from adjacent ends of said trunk portions such that said interior regions of said leg portions of said inner tube structure communicate with said interior region of said trunk portion of said inner tube structure.

3. An implantable vascular graft according to claim 2, wherein said trunk portion or one of said leg portions has said reinforced portion.

4. An implantable vascular graft according to claim 1, wherein said outer tube structure has an outer surface to which said first or second reinforcing material is stitched.

5. An implantable vascular graft according to claim 1, wherein said inner tube structure has an inner surface to which said reinforcing material is stitched.

6. An implantable vascular graft according to claim 1, wherein said reinforcing material is located between said outer and inner tubes.

7. An implantable vascular graft according to claim 1, wherein said inner tube is formed of a PTFE material.

8. An implantable vascular graft according to claim 1, wherein said textile material is knitted, weaved or braided.

9. The implantable vascular graft of claim 1, wherein the bonding material is made of PTFE.

10. The implantable vascular graft of claim 1, wherein the bonding material is an adhesive material.

11. The implantable vascular graft of claim 1, wherein the bonding material transitions from the first state to the second state upon application of heat.

12. The implantable vascular graft of claim 1, wherein securing the outer tube structure to said inner tube structure results in deformation of one of the outer or inner tube structures thereby producing equivalent deformation in the other of the structures.

13. The implantable vascular graft of claim 1, further comprising a reinforcing material, the reinforcing material being incorporated into at least one of the outer or inner tube structures.

* * * * *